US006692762B2

(12) United States Patent
Cain et al.

(10) Patent No.: US 6,692,762 B2
(45) Date of Patent: Feb. 17, 2004

(54) PROCESS FOR THE PREPARATION OF MATERIALS WITH A HIGH CONTENT OF LONG CHAIN POLYUNSATURATED FATTY ACIDS

(75) Inventors: Frederick William Cain, Wormerveer (NL); Stephen Raymond Moore, Sharnbrook (GB); Gerald Patrick McNeill, Sharnbrook (GB); Olga Cornelia Zwemmer, Wormerveer (NL)

(73) Assignee: Loders Croklaan B.V. (NL)

( * ) Notice: Subject to any disclaimer, the term of this patent is extended or adjusted under 35 U.S.C. 154(b) by 0 days.

(21) Appl. No.: 09/500,475

(22) Filed: Feb. 9, 2000

(65) Prior Publication Data

US 2003/0013164 A1 Jan. 16, 2003

Related U.S. Application Data

(63) Continuation of application No. 09/068,154, filed as application No. PCT/EP96/05024 on Nov. 12, 1996, now Pat. No. 6,184,009.

(30) Foreign Application Priority Data

Nov. 14, 1995 (EP) .............................................. 95308228

(51) Int. Cl.$^7$ ...................... A61K 9/06; A61K 31/231; A23D 7/00; A23D 9/00
(52) U.S. Cl. ...................... 424/439; 426/601; 426/603; 514/549
(58) Field of Search .................... 424/439; 514/549; 554/224; 426/601, 603; 435/135

(56) References Cited

U.S. PATENT DOCUMENTS

| 4,164,505 A | 8/1979 | Krajca |
| 4,792,449 A | 12/1988 | Ausman |
| 5,017,614 A | 5/1991 | Pariza et al. |
| 5,026,553 A | 6/1991 | Swinney |
| 5,288,619 A | 2/1994 | Brown et al. |
| 5,674,901 A | 10/1997 | Cook et al. |

FOREIGN PATENT DOCUMENTS

| EP | 442558 | 8/1991 |
| EP | 579901 | 1/1994 |
| WO | 90/09110 | 8/1990 |
| WO | 94/17672 | 8/1994 |

*Primary Examiner*—Edward J. Webman
(74) *Attorney, Agent, or Firm*—Morgan Lewis & Bockius LLP

(57) ABSTRACT

Compositions comprising glycerides containing conjugated linoleic acid moieties. These glycerides are prepared by an enzymatic conversion process which is selective to provide specific isomers, advantageously the $cis^9$, $trans^{11}$ and $trans^{10}$, $cis^{12}$ linoleic acid isomers or vice versa. The compositions may be blended with complementary fats and may be used in foods, food supplements and pharmaceutical compositions.

4 Claims, No Drawings

PROCESS FOR THE PREPARATION OF MATERIALS WITH A HIGH CONTENT OF LONG CHAIN POLYUNSATURATED FATTY ACIDS

This is a continuation of application Ser. No. 09/068,154, filed Sep. 30, 1998 now U.S. Pat. No. 6,184,009 as a 371 filing of PCT/EP96/05024, filed Nov. 12, 1996.

The beneficial effects of conjugated long chain polyunsaturated fatty acids in food products for animals or humans have been recognised in the prior art.

EP 411.101 e.g, discloses, that compositions containing free conjugated linoleic acid (=CLA), such as 9.11-dienic and 10.12-dienic fatty acids or non-toxic salts thereof can be used to preserve products by inhibiting mould growth. According to this EP'101 the free acids are prepared by reacting linoleic acid with a protein, capable of effecting the transformation of linoleic acid to the desired acid forms at temperatures up to 85° C. The CLA obtained contains both the 9.11 and 10.12-octadecadienoic acids and active isomers therefrom. Because of cis/trans-isomerism above CLA's can contain 8 different isomers, i.e. $cis^9$-$cis^{11}$; $cis^9$-$trans^{11}$; $trans^9$-$cis^{11}$; $trans^9$-$trans^{11}$; $cis^{10}$-$cis^{12}$; $cis^{10}$-$trans^{12}$; $trans^{10}$-$cis^{12}$ and $trans^{10}$-$trans^{12}$. From those isomers the $cis^9$-$trans^{11}$ and $trans^{10}$-$cis^{12}$ are the most abundant, while their concentrations are about equal. It is generally believed, that those two most abundant isomers are responsible for the beneficial effects of the compositions, containing CLA's.

According to EP 440.325 CLA's can be applied as "metal chelator" in natural foods. The CLA's contain 9.11 and 10.12-octadecadienoic acid, salts or other derivatives thereof. The free acids can be prepared by e.g. an enzymic treatment, using $\Delta^{12}$ cis $\Delta^{11}$ trans isomerase, of linoleic acid.

In U.S. Pat. No. 5,430,066 it is disclosed, that CLA's can be applied in foods for preventing weight loss, reduction in weight gain or anorexia in animals or humans. Also disclosed is, that these CLA's can alleviate the adverse catabolic effects of a product from the immune-system, in particular from interleukin-1.

From U.S. Pat. No. 5,428,072 it is known, that CLA's can be used for the increase of the efficiency of feed conversion to body weight in an animal.

Shantha c.s disclosed in J. of AOAC Intern 76 (3) 1993, p. 644–649 that CLA-isomers are potential anticarcinogens.

According to Fogerty c.s in Nutrition Reports Intern 38 (5), 1988, p. 937–944 $cis^9$-$trans^{11}$ linoleic acid can be used in various foods or human milk.

U.S. Pat. No. 4,164,505 discloses a process, wherein unconjugated unsaturated fattty acids are isomerised into conjugated unsaturated fatty acids by a treatment with base. As a result of this process a kinetically controlled reaction-mixture will be obtained, wherein the double bonds are conjugated but distributed over the whole carbon chain of the polyunsaturated fatty acids. Therefore this process does not result in organic materials, wherein the two most abundant conjugated polyunsaturated fatty acid moieties L1 and L2 are present in a weight-ratio $$\frac{L_1}{L_2} = 2.3 - 99,$$

as we aim for as a result of our process.

Above prior art methods and products do have a number of drawbacks. E.g. the methods for the preparation of the CLA's according to above prior art cannot be applied on a commercial scale, e.g. because the yields of the products are very limited. Moreover the products obtained always will have one specific ratio between the $cis^9$-$trans^{11}$/$trans^{10}$-$cis^{12}$ isomers (in general about 1.0). Therefor compositions with an other ratio than 1.0 cannot be obtained. As the effectiveness of the two isomers for specific purposes are different it is highly desirable to have the opportunity to make CLA's, wherein the ratio $$\frac{cis^9 - trans^{11}}{trans^{10} - cis^{12}}$$

can be chosen freely, depending on the conditions applied during the process.

Therefore our invention concerns a new process for the preparation of CLA's, wherein the ratio $$\frac{cis^9 - trans^{11}}{trans^{10} - cis^{12}}$$

can be chosen freely. This new method can be applied for the preparation both of new CLA-compositions and known CLA-compositions.

So our inventions concerns a process for the preparation of materials, containing conjugated unsaturated fatty acid moieties, wherein a material, containing at least 5 wt % of conjugated polyunsaturated fatty acid moieties, comprising at least two different isomers $L_1$ and $L_2$ in a weight ratio $L_1:L_2=X_A$, is subjected to an enzymic conversion, selected from one of the following conversions:
(i) free fatty acids with:
   (a) mono- or polyalcohols, or
   (b) mono, -di-triglycerides, or
   (c) alkylesters, or
   (d) phospholipids
(ii) mono, -di- or triglycerides with:
   (a) water, or
   (b) mono- or polyalcohols, or
   (c) alkylesters, or
   (d) phospholipids
(iii) phospholipids with:
   (a) water, or
   (b) alkylesters, or
   (c) other phospholipids, or
   (d) mono- or polyols
(iv) alkylesters, or wax-esters with:
   (a) water, or
   (b) mono- or polyols, or
   (c) free fatty acids, or
   (d) phospholipids,
wherein an enzyme is applied, that has the ability to discriminate between $L_1$ and $L_2$, which conversion results in a mixture of at least two products (I) and (II), from which at least one product (I) or (II) contains $L_1$ and $L_2$ in a weight-ratio $X_B$, $X_B$ being at least 1.1 $X_A$, preferably at least 1.2 $X_A$, most preferably at least 1.3 $X_A$, and wherein $L_1$ and $L_2$ are different isomers of polyunsaturated fatty acids with at least two unsaturations and at least 18 carbon atoms.

Enzymes that can be applied for the enzymic conversion are e.g. *Geotrichum candidum* and *Candida rugosa* and phospholipases.

As indicated above many different types of reactants can be applied for the enzymic conversion. It was found, that very good results are obtained, when the conversion is performed on a mixture of free fatty acids, containing at least 5 wt %, preferably at least 10 wt %, most preferably at least 15 wt % of conjugated polyunsaturated fatty acids and a phospholipid or a mono, -di- or triglyceride;

Preferred starting materials, applicable in the process according to the invention have a weight ratio $X_A$ (ie $L_1:L_2$) of about 1.0.

According to another embodiment of the invention water or glycerol, mixed with a mono, -di- or triglyceride could be converted as well. In this instance the glyceride material is the reactant having at least 5 wt % conjugated polyunsaturated fatty acids in it.

Although above process can be applied on any starting material, wherein $L_1$ and $L_2$ can be chosen from all long chain polyunsaturated fatty acid moieties with at least two unsaturations and 18 or more carbon atoms, as long as the long chain polyunsaturated acids present are present in different cis/trans-isomeric forms, it is preferred that $L_1$ and $L_2$ are $cis^9$ $trans^{11}$ and $trans^{12}$ $cis^{12}$-linoleic acid (or vice versa)

The process of the invention can be applied for the preparation of known compounds, however also novel compositions can be obtained by using this process. These novel compounds (compositions) have unexpected properties, because of the weight-ratio $L_1:L_2$ that occurs in these compositions. Therefore our invention also concerns novel organic materials, which-materials contain at least 1 wt % of conjugated polyunsaturated fatty acid moieties with a chain length of at least 18 C-atoms, wherein the conjugated polyunsaturated fatty acid moieties at least comprise two isomers $L_1$ and $L_2$ in a weight-ratio:

$$\frac{L1}{L2} = 2.3 - 99,$$

preferably 4–20, most preferably 8–15 $L_1$ being the most abundant and $L_2$ being the second most abundant conjugated polyunsaturated fatty acid moiety in the material, while $L_1$ and $L_2$ are different isomers of polyunsaturated fatty acids with at least two unsaturations and at least 18 carbon atoms.

The organic materials, that can be obtained can be: either a mixture of free fatty acids, a mixture of wax-esters, a mixture of low alkylesters, a mixture of monoglycerides, or, diglycerides or triglycerides or mono, -di- and triglycerides, or a mixture of phospholipids, or a mixture of one or more components of said mixtures.

In the novel organic materials $L_1$ and $L_2$ can both be selected from $cis^9,trans^{11}$ and $trans^{10},cis^{12}$-linoleic acid.

In many instances the starting material for our process will be an animal-derived material, such as a fish oil. However it is also possible to use vegetable oils as starting material. By using such vegetable oils the products of the conversion are novel over any product known in the prior art, as vegetable oils contain small amounts of specific components, which are not present in e.g. the fish oils, and which are indicative for the vegetable source the oil is derived of. So organic materials, derived from vegetable oils, having at least two conjugated polyunsaturated fatty acids moieties $L_1$ and $L_2$, wherein $L_1$ is the most abundant and $L_2$ is the second most abundant conjugated polyunsaturated fatty acid moiety, wherein $L_1$ and $L_2$ are present in a weight-ratio of 1.5–25, preferably 4–20, most preferably 8–15, while the total amount of conjugated polyunsaturated fatty acid moieties in the organic material is at least 1 wt %, and wherein $L_1$ and $L_2$ are different isomers of polyunsaturated fatty acids with at least two unsaturations and at least 18 carbon atoms, are considered to be novel over any prior art product, derived from a non-vegetable source.

As is well-known from the prior art organic materials containing large amounts of polyunsaturated fatty acids are very sensitive for oxygen. Therefore we prefer to add an effective amount of an oxidation stabilizer, selected from the group, consisting of: natural or synthetic tocopherols, TBHQ, BHT, BHA, free radical scavengers, propylgallate, ascorbylesters of fatty acids and enzymes with anti-oxidant properties.

Although our organic materials could be applied as such, it is often preferred to use them as a blend with a complementary fat. Therefore our invention also concerns blends of an organic material and a complementary fat, wherein the blend comprises:

0.3–95 wt %, preferably 2–80 wt %, most preferably 5–40 wt % of the organic material, obtainable by the process according to claims 1–6, or the organic material according to claims 7–11, and 99.7–5 wt %, preferably 98–20 wt %, most preferably 95–60 wt % of a complementary fat, selected from: cocoa butter, cocoa butter equivalents, palm oil or fractions thereof, palmkernel oil or fractions thereof, interesterified mixture of said fats or fractions thereof, or liquid oils, selected from: sunflower oil, high oleic sunflower oil, soybean oil, rapeseed oil, cottonseed oil, fish oil, safflower oil, high oleic safflower oil, maize oil and MCT-oils.

Above blends of organic material and complementary fat preferably display a solid fat content (NMR-pulse, unstabilised) of 0–85, more preferably 10–70, most preferably 20–60 at 5° C. and <30, more preferably <20, most preferably < at 35° C.

Part of the invention are also food products and animal feed, containing a fatphase, wherein the fatphase contains an effective amount of the product, obtainable by the process of claims 1–5 or the organic material of claims 6–10, or the blend of claims 11–12. The food products are suitably selected from the group consisting of: spreads, margarines, creams, dressings, mayonnaises, ice-creams, bakery products, infant food, chocolate, confectionery, sauces, coatings, cheese and soups.

However also food supplements and pharmaceutical products can be obtained by using our fats or blends. Therefore foodsupplements or pharmaceutical products, that are in the form of capsules or other forms, suitable for enteral or parenteral application and that comprise a product obtainable according to the process of the invention or an organic material or a blend, according to the invention, are also part of the invention.

*LIST OF ABBREVIATIONS AND CODES USED IN THE EXAMPLES*

*CCB* = Cocoa butter.

*POf37* = Partially hardened palm oil olein fraction melting point of 37° C.

*CN* = Coconut oil.

*CNs* = Coconut oil stearin fraction.

*nPOm* = Wet fractionated palm oil mid fraction.

*df(PO)f* = Dry fractionated palm oil olein fraction.

*HS* = *Hardstock* = The stearin fraction of a chemically interesterified blend of fully hardened palm oil and a fully hardened palm kernel olein fraction.

*S* = Sunflower oil.

*PO* = Palm oil.

*in* = Interesterified.

*TBHQ* = Mono-tertbutylhydroquinone

Analytical Methods

Fatty acid compositions were determined by fatty acid methyl ester gas chromatography (FAME GC) using the method given in JAOCS Vol 71 no 12 page 1321.

Partial glyceride contents were determined by-silica gel high performance liquid chromatography (HPLC) using an evaporative light scattering detector with 12, hydroxy iso-octane as an internal standard.

Free fatty acid contents were determined by titration against standard sodium hydroxide and are expressed as % oleic acid.

EXAMPLES

Example 1

Fifty grams of linoleic acid (95% pure) were added to a solution of 15 grams of NaOH in 290 grams of ethylene glycol. The mixture was heated at 180° C. under an inert atmosphere for 2 hours. The reaction mixture was cooled, the pH was adjusted to 4 with HCl and extracted with two 50 ml portions of hexane. The combined hexane extract was washed with three 25 ml portions of 5% NaCl and dried over $Na_2SO_4$ and the solvent was removed by rotary evaporation. The fatty acid distribution as determined by FAME GC showed the product contained 91.8% of conjugated linoleic acid (CLA) of which 49.7% was the cis 9, trans 11 isomer and 50.3 % was the trans 10, cis 12 isomer. The CLA product was stored at −20° C. under a nitrogen atmosphere.

In this process 2.786 grams of octanol were weighed into a glass vessel with 6.0 grams of the mixed CLA isomers prepared as described above. To this was added 6 ml of a solution TBHQ in distilled water (0.2 mg/ml) and 12 ml of a solution of *Geotrichum candidum* lipase in distilled water (5 mg/ml). The reaction mixture was adjusted to 25° C. and agitated by a orbital shaker under nitrogen. After 72 hours reaction time a sample was removed and a conversion of 35.1% was determined. Unreacted fatty acids were separated from fatty acid octylesters by thin layer chromatography (TLC). The CLA in the octyl ester fraction was found to be composed of 97.6% cis 9, trans 11 isomer and 2.4% trans 10, cis 12 isomer. The CLA in the free fatty acid fraction was found to be composed of 29.3% cis 9, trans 11 isomer and 70.7% trans 10, cis 12 isomer.

Example 2

Mixed CLA isomers were prepared as described in example 1. The results of the gas chromatographic analysis of the fatty acid methyl esters were as follows. The product contained 89.9% CLA of which 49.7% was the cis 9, trans 10 isomer and 50.3% was the trans 10, cis 12 isomer.

A product was made according to the following process. Twenty mg of *Geotrichum candidum* lipase (1% lipase based on acid) were dissolved in 6.0 ml of distilled and de-gassed water. This solution was de-gassed again. Two grams of mixed CLA isomers prepared as described in example 1, were mixed with 0.9288 grams of octanol (1:1 mole-ratio acid:alcohol) and added to the lipase solution. One drop of tocomix antioxidant was added to this mixture. The temperature of the reaction mixture was adjusted to 35° C. and agitated by magnetic stirring under nitrogen. After 24 hours reaction time and a conversion of 21% a sample was removed and unreacted fatty acids were separated from fatty acid octyl esters by thin layer chromatography (TLC). The CLA in the octyl ester fraction was found to be composed of 94% cis 9, trans 11 isomer and 6% trans 10, cis 12 isomer.

The CLA in the free fatty acid fraction was found to be composed of 38% cis 9, trans 11 isomer and 62% trans 10, cis 12 isomer.

Example 3

Mixed CLA isomers which were prepared as described in example 2, were used in this example.

A product was made according to the process described in example 2. After 96 hours of reaction time and a conversion of 53% a sample was removed and unreacted fatty acids were separated from fatty acid octyl esters by thin layer chromatography (TLC). The CLA in the octyl ester fraction was found to be composed of 81% cis 9, trans 11 isomer and 19% trans 10, cis 12 isomer. The CLA in the free fatty acid fraction was found to be composed of 15% cis 9, trans 11 isomer and 85% trans 10, cis 12 isomer.

Example 4

A product was made according to the following process. Octanol (0.4644 grams) and 1.0 gram of the mixed CLA isomers prepared as described in example 1, were weighed into a glass vessel. To this was added 1 ml of a solution TBHQ in distilled water (0.2 mg/ml) and 2 ml of a solution of *Candida rugosa* lipase in distilled water (5 mg/ml). The reaction mixture was adjusted to 25° C. and agitated by a orbital shaker under nitrogen. After 30 minutes reaction time a sample was removed and a conversion of 43.4% was determined. Unreacted fatty acids were separated from fatty acid octylesters by thin layer chromatography (TLC). The CLA in the octyl ester fraction was found to be composed of 90.7% cis 9, trans 11 isomer and 9.3% trans 10, cis 12 isomer. The CLA in the free fatty acid fraction was found to be composed of 21.5% cis 9, trans 11 isomer and 78.5% trans 10, cis 12 isomer.

Example 5

A product was made according to the process described in example 4. After 45 minutes reaction time a sample was removed and a conversion of 48.3% was determined. Unreacted fatty acids were separated from fatty acid octylesters by thin layer chromatography (TLC). The CLA in the octyl ester fraction was found to be composed of 84.8% cis 9, trans 11 isomer and 15.2% trans 10, cis 12 isomer. The CLA in the free fatty acid fraction was found to be composed of 10.1% cis 9, trans 11 isomer and 89.9% trans 10, cis 12 isomer.

Example 6

A solution of 600 grams of NaOH in 6 kilograms of ethylene glycol was added to two kilograms of sunflower oil. The mixture was stirred and heated at 180° C. under an inert atmosphere for 3 hours. The reaction mixture was cooled to about 90–95° C. whilst being stirred thus avoiding precipitation of solid soap. A solution of 1280 mls of HCl in 8 kilograms of demineralised water was added slowly to the reaction mixture. Then the stirring was stopped and the mixture was allowed to settle in an inert atmosphere. The pH was adjusted to 4 with HCl. The aqueous phase was separated from the oil phase. The oil phase was washed at 90° C. with two 1 liter portions of 5% NaCL and one 2 liter portion of hot demineralised water then dried at 100° C. under vacuum. The dried oil phase was cooled to 50–60° C. blanketed with nitrogen and filtered. The fatty acid composition of the product, as determined by FAME GC, contained 61.9% of conjugated linoleic acid (CLA) of which 48.9% was the cis 9, trans 11 isomer and 51.1% was the trans 10, cis 12 isomer. The product (=SOCLA) was stored at −20° C. under a nitrogen atmosphere.

In this process 0.986 grams of glycerol were weighed into a glass vessel with 1.0 gram of SOCLA prepared as described above. To this were added 150 μls of distilled water and 100 mgs of *Geotrichum candidum* lipase. The reaction mixture was adjusted to 35° C. and agitated by a orbital shaker (250 rpm) under nitrogen. After 8 hours reaction time a sample was removed and a conversion of 16.6% was determined. The partial glyceride content of this reaction mixture as determined by HPLC. was 9.6% of monoglycerides, 3.8% of diglycerides and 3.2% of triglycerides. Unreacted fatty acids (83.4%) were separated from mono-, di- and triglycerides by thin layer chromatography (TLC). The CLA in the monoglyceride fraction was found to be composed of 66.8% cis 9, trans 11 isomer and 33.2% trans 10, cis 12 isomer. The CLA in the diglyceride fraction was found to be composed of 80.0% cis 9, trans 11 isomer and 20.0% trans 10, cis 12 isomer. The CLA in the triglyceride fraction was found to be composed of 77.9% cis 9, trans 11 isomer and 22.1% trans 10, cis 12 isomer. The CLA in the free fatty acid fraction was found to be composed of 45.7% cis 9, trans 11 isomer and 54.3% trans 10, cis 12 isomer.

Example 7

SOCLA was prepared as described in example 6. The results of the gas chromatography analysis of the fatty acid methyl esters were as follows. The product contained 63.8% CLA of which 48.9% was the cis 9, trans 10 isomer and 51.1% was the trans 10, cis 12 isomer.

A product was made according to the following process. Glycerol (400 grams) and 401.5 grams of SOCLA were weighed into a water jacketed glass reaction vessel. To this were added 44.4 grams of distilled water and 0.8 grams of *Candida rugosa* lipase. The reaction mixture was adjusted to 35° C. and agitated by overhead stirring (250 rpm) under nitrogen. After 5 hours reaction time a sample was removed and a conversion of 42% was determined. Then the reaction was stopped by heating up the reaction mixture to 80° C. The aqueous phase was separated from the oil phase by extracting the emulsion with hexane. The hexane was removed by rotary evaporation. Unreacted fatty acids were separated from mono-, di- and triglycerides by thin layer chromatography (TLC)and analysed by gas chromatography. The results of these FAME analysis are listed in table 1a. The unreacted free fatty acids (58%) were separated from the mono-, di and triglycerides by molecular distillation. FAME GC and HPLC analyses were done on the two fractions after molecular distillation. The results of these analyses are listed in table 1b.

Example 8

CLA triglycerides were prepared from SOCLA. A re-esterification reaction was performed containing SOCLA (428 g), glycerol (47 g) and *Rhizomucor miehei* supported lipase (24 g). The reaction was performed in a 1 l jacketed vessel and heated to 60° C., with continuous stirring, in an inert atmosphere. Samples were removed at regular intervals and the levels of FFA determined; only 6% FFA remained in the-reaction mixture after 45.5 h. The reaction was then stopped by heating the reaction mixture to 80° C. The inactivated lipase was removed by means of filtration using a Whatman no. 54 filter and the oil recovered. HPLC analysis of a sample of the oil indicated the presence of low levels of 1,3- and 1,2-diglycerides, 5.4% and 1.9%, respectively.

CLA partial glycerides, enriched in the 10t,12c-isomer, were prepared by the selective hydrolysis of CLA triglycerides. The hydrolysis reaction was performed in a 1 l jacketed vessel containing CLA triglycerides (395 g), distilled water (395 g) and *Candida rugosa* lipase (0.8 g). The reaction mixture was heated to 35° C., with continuous stirring, in an inert atmosphere and samples were removed for FFA analysis at regular intervals. At 60% conversion (after 1 h 10 min) the reaction was stopped by heating to 80° C. and the oil and aqueous phases allowed to separate. The oil phase was recovered and extracted with hexane and, subsequently, the solvent removed by rotary evaporation. A sample of the oil was separated into component FFA and partial glycerides (MG, DG and TG) by TLC (mobile phase consisted: 60 diethyl ether, 40 hexane and 1 formic acid, by vol.) and the corresponding bands analysed by GC. FAME GC analyses of the enriched oil are listed in below. HPLC analysis indicated the presence of 1,3-diglycerides (6.5%), 1,2-diglycerides (5.2%) and monoglycerides (1.1%). Percentage CLA Isomers Following 60% Hydrolysis of CLA Triglycerides Using *C. rugosa* Lipase.

| CLA isomers | Ratio of isomers | | | |
|---|---|---|---|---|
| | FFA | TG | DG | MG |
| 9c,11t- and 9t,11c | 30.1 | 18.1 | 17.0 | 18.1 |
| 10t,12c | 19.0 | 42.1 | 47.0 | 38.1 |

Molecular distillation of the oil enabled separation of the free fatty acids (197 g) and partial glycerides (129 g). FFA analysis of the partial glyceride fraction indicated the presence of low levels of FFA (8.2%) and HPLC analysis indicated the presence of 35.8% diglycerides (20.6% 1,3- and 15.2% 1,2-) and 0.9% monoglycerides. Total FAME GC analysis of this fraction indicated an enrichment of the 10t, 12c-CLA isomer (46.5% 10t,12c- and 19.3% 9c,11t-)

Example 9

Partial glycerides rich in the cis 9, trans 11 isomer of CLA as produced in example 7 were re-esterified to form a triglyceride rich fat. 11.6 g of the partial glycerides as produced in example 7 were mixed with 6.03 g of free fatty acids, produced by complete hydrolysis of sunflower oil, and 0.54 g of *Rhizomucor miehei* lipase immobilised onto Duolite. The mixture was stirred in an open glass vial at 55° C. for 48 hours with nitrogen blowing across the surface. The partial glyceride content-of the resultant blend as determined by HPLC was 75% triglyceride 13% FFA and 11.6% diglycerides. The product was alumina treated to remove residual free fatty acid. The triglycerides contained 36.6% CLA of which 74.6% was the cis 9, trans 11 isomer and 25.4% was the trans 10, cis 12 isomer.

Example 10

Partial glycerides rich in the trans 10, cis 12 isomer of CLA as produced in example 8 were re-esterified to form a triglyceride rich fat. 12.6 g of the partial glycerides as produced in example 8 were mixed with 2.03 g of free fatty acids, produced by complete hydrolysis of sunflower oil, and 0.52 g of *Rhizomucor miehei* lipase immobilised onto Duolite. The mixture was stirred in an open glass vial at 55° C. for 48 hours with nitrogen blowing across the surface. The partial glyceride content of the resultant blend as determined by HPLC was 82% triglyceride 12% FFA and 5.6% diglycerides. The product was alumina treated to remove residual free fatty acid. The triglycerides contained 56.8% CLA of which 30.3% was the cis 9, trans 11 isomer and 69.3% was the trans 10, cis 12 isomer.

Example 11

0.50 g of CLA acids, as produced in example 1, were mixed with 4.54 g sunflower oil, 0.09 g of *Candida rugosa* Lipase (OF) and 0.008 g of water. The mixture was stirred under a blanket of nitrogen at 30° C. in a glass jacketed vessel fitted with a magnetic stirrer.

After 6 hours a sample was removed and immediately heated to 80° C. to inactivate the enzyme. The partial glycerides and free fatty acids were removed by treatment with basic alumina. The fatty acid distribution in the remaining triglycerides was determined by FAME GC. The incorporation of CLA into triglyceride molecules was 2.1% of which 71.4% was the cis 9, trans 11 isomer and 28.6% was the trans 10, cis 12 isomer.

Example 12

Triglycerides rich in the cis 9, trans 11 isomer which were prepared as described in example 9, were used for this example. Blends were made of triglycerides rich in the cis 9, trans 11 isomer (=C9T11) and a complementary fat/fat blend for the following applications:

| Application | Reference | Blends inside the patent |
|---|---|---|
| Chocolate | Cocoa butter | Cocoa butter/C9T11 99/1 |
| Bakery | POf37/df(PO)f 40/60 | POf37/df(PO)f/C9T11 40/50/10 |
| Ice cream coatings | Coconut oil | CN/CNs/C9T11 90/5/5 |
| Ice cream | PO | PO/C9T11 90/10 |
| Non dairy creams | nPOm/df(PO)f 40/60 | nPOm/df(PO)f/C9T11 40/40/20 |
| Health margarines/ Health spreads | HSB1/S 13/87 | HSB1/S/C9T11 13/77/10 |
| Confectionery fillings | nPOm/df(PO)f 60/40 | nPOm/dt(PO)f/C9T11 60/25/15 |
| Mayonnaise/Sauces | S | S/C9T11 95/5 |
| Dressings | S | S/C9T11 95/5 |

The range of N-values of the references and measured N-values for the blends are listed in table 2.

Example 13

Triglycerides rich in the trans 10 cis 12 isomer which were prepared as described in example 10, were used for this example. Blends were made of triglycerides rich in the trans 10, cis 12 isomer (=T10C12) and a complementary fat/fat blend for the following applications:

| Application | Reference | Blends inside the patent |
|---|---|---|
| Chocolate | Cocoa butter | Cocoa butter/T10C12 99/1 |
| Bakery | POf37/df(PO)f 40/60 | POf37/df(PO)f/T10C12 40/50/10 |
| Ice cream coatings | Coconut oil | CN/CNs/T10C12 90/5/5 |
| Ice cream | PO | PO/T10C12 90/10 |
| Non dairy creams | nPOm/df(PO)f 40/60 | nPOm/df(PO)f/T10C12 40/40/20 |
| Health margarines/ Health spreads | HSB1/S 13/87 | HSB1/S/T10C12 13/77/10 |
| Confectionery fillings | nPOm/df(PO)f 60/40 | nPOm/df(PO)f/T10C12 60/25/15 |
| Mayonnaise/Sauces | S | S/T10C12 95/5 |
| Dressings | S | S/T10C12 95/5 |

The range of N-values of the references and measured N-values for the blends are listed in table 3.

Example 14

Spreads incorporating glycerides rich in the cis 9, trans 11 isomer of CLA, as made in example 7, were prepared according to the following recipe:

| Fat Phase | |
|---|---|
| Fat Blend | 40% |
| Hymono 7804 | 0.3% |
| Colour (2% β-carotene) | 0.02% |
| Total | 40.32% |
| Aqueous Phase (to pH 5.1) | |
| Water | 56.44% |
| Skimmed Milk Powder | 1.5% |
| Gelatin (270 bloom) | 1.5% |
| Potassium Sorbate | 0.15% |
| Citric Acid Powder | 0.07% |
| Total | 59.66% |

In above recipe two different fat blends were applied. The fat blend for the reference was HS/Sunflower oil 13/87 and the fat blend according to the invention was prepared by interesterification of 76.7 g of glycerides rich in cis9, trans 11 CLA acids as prepared in example 7, with 1423 g of sunflower oil using 74 g of *Rhizomucor miehei* immobilised onto Duolite as catalyst. The reaction was carried out at 60° C. for 7 hours. The enzyme was removed by filtration. The resultant product rich in triglycerides containing cis9, trans 11 CLA acids was silica treated to remove partial glycerides and was then blended with hardstock as follows:

HS/in(Sunflower oil/C9T11 CLA) 13/87

The FAME GC results of the in(Sunflower oil/C9T11 CLA) and the blend with the hardstock are listed in table 4.

The spreads were processed according to the following procedure:

3 kg of material was prepared and processed.

A micro-votator processing line was set up as follows:

| Premix conditions | Stirrer Speed 60 rpm Temperature 60° C. |
|---|---|
| pump | Proportioning pump set at 80% (40 g/min.). |
| A₁ conditions | Shaft speed 1000 rpm Temperature set at 8° C. |
| C₁ conditions | Shaft speed 1000 rpm Temperature set to 10° C. |
| A₂ conditions | Shaft Speed 1000 rpm Temperature set to 10° C. |
| C₂ conditions | Shaft speed 1000 rpm Temperature set to 13° C. |

The aqueous phase was prepared by heating the required amount of water to approximately 80° C. and then, using a Silverson mixer, slowly mixing in the ingredients. The pH of the system was adjusted to 5.1 by adding 20% Lactic acid solution as required.

A premix was prepared by stirring the fat phase in the premix tank and then slowly adding in the aqueous phase. When addition was complete, the mix was stirred for a further 5 minutes before pumping through the line. When the process had stabilised (around 20 minutes), product was collected for storage and evaluation. The typical process conditions were as follows:

| Sample | $A_{1\,Exit}$ (° C.) | $C_{1\,Exit}$ (° C.) | $A_{2\,Exit}$ (° C.) | $C_{2\,Exit}$ (° C.) | Line Pressure (bar) |
|---|---|---|---|---|---|
| Reference | 16.1 | 17.6 | 15.0 | 18.0 | 3.3 |
| HS/in(S/C9T11) 13/87 | 15.4 | 16.7 | 15.3 | 17.8 | 4.1 |

Very good oil continuous low fat spreads were produced using this system for both the reference and the CLA product.

The spreads were evaluated after 5 days storage at 5° C. and 20° C., for hardness using a cone penetrometer, electrical conductivity and for the plasticity of the product by formation of a collar using a 2 mm steel rod.

| | 5° C. | | | 20° C. | | |
|---|---|---|---|---|---|---|
| Sample | C-Value | Conductivity | Collar | C-value | Conductivity | Collar |
| Reference | 170 | $10^{-6}$ | I | 140 | $10^{-6}$ | I |
| HS/in(S/C9T11) | 170 | $10^{-8}$ | I | 130 | $10^{-8}$ | I |

All samples spread very easily on grease-proof paper, with no obvious signs of water loss.

Example 15

Spreads incorporating glycerides rich in the trans 10, cis 12 isomer of CLA, as made in example 8, were prepared according to the following recipe:

| Fat Phase | |
|---|---|
| Fat Blend | 40% |
| Hymono 7804 | 0.3% |
| Colour (2% β-carotene) | 0.02% |
| Total | 40.32% |
| Aqueous Phase (to pH 5.1) | |
| Water | 56.44% |
| Skimmed Milk Powder | 1.5% |
| Gelatin (270 bloom) | 1.5% |
| Potassium Sorbate | 0.15% |
| Citric Acid Powder | 0.07% |
| Total | 59.66% |

In above recipe two different fat blends were applied. The fat blend for the reference was HS/Sunflower oil 13/87 and the fat blend according to the invention was a blend of the hardstock with glycerides rich in the trans 10, cis 9 isomer which were prepared as described in example 8 and sunflower oil, HS/Sunflower oil/T10C12 CLA 13/82/5

The FAME results of the T10C12 CLA are listed in table 4.

The spreads were processed according to the following procedure:

3 kg of material was prepared and processed.

A micro-votator processing line was set up as follows:

| Premix conditions | Stirrer Speed 60 rpm Temperature 60° C. |
|---|---|
| pump | Proportioning pump set at 80% (40 g/min.). |
| $A_1$ conditions | Shaft speed 1000 rpm Temperature set at 8° C. |
| $C_1$ conditions | Shaft speed 1000 rpm Temperature set to 10° C. |
| $A_2$ conditions | Shaft Speed 1000 rpm Temperature set to 10° C. |
| $C_2$ conditions | Shaft speed 1000 rpm Temperature set to 13° C. |

The aqueous phase was prepared by heating the required amount of water to approximately 80° C. and then, using a Silverson mixer, slowly mixing in the ingredients. The pH of the system was adjusted to 5.1 by adding 20% Lactic acid solution as required.

A premix was prepared by stirring the fat phase in the premix tank and then slowly adding in the aqueous phase. When addition was complete, the mix was stirred for a further 5 minutes before pumping through the line. When the process had stabilised (around 20 minutes), product was collected for storage and evaluation.

The typical process conditions were as follows:

| Sample | $A_{1\,Exit}$ (° C.) | $C_{1\,Exit}$ (° C.) | $A_2$ Exit (° C.) | $C_{2\,Exit}$ (° C.) | Line Pressure (bar) |
|---|---|---|---|---|---|
| Reference | 16.1 | 17.6 | 15.0 | 18.0 | 3.3 |
| HS/S/T10C12 13/82/5 | 16.4 | 17.0 | 16.5 | 17.6 | 4.5 |

Very good oil continuous low fat spreads were produced using this system for both the reference and the CLA product.

The spreads were evaluated after 5 days storage at 5° C. and 20° C., for hardness using a cone penetrometer, electrical conductivity and for the plasticity of the product by formation of a collar using a 2mm steel rod.

| | 5° C. | | | 20° C. | | |
|---|---|---|---|---|---|---|
| Sample | C-Value | Conductivity | Collar | C-value | Conductivity | Collar |
| Reference | 170 | $10^{-5}$ | I | 140 | $10^{-5}$ | I |
| HS/S/T10C12 | 160 | $10^{-5}$ | I | 130 | $10^{-5}$ | I |

All samples spread very easily on grease-proof paper, with no obvious signs of water loss.

Example 16

Ranch style dressings incorporating glycerides rich in the cis 9, trans 11 isomer of CLA, as made in example 7, were prepared according to the following recipe:

|  | wt % |
|---|---|
| Liquid oil | 25.0 |
| Maltodextrin | 20.0 |
| Dried egg yolk | 0.8 |
| Xanthum gum | 0.4 |
| Vinegar | 5.0 |
| Water | 48.8 |

In above recipe two different liquid oils were applied. The liquid oil for the reference was Sunflower oil and the liquid oil according to the invention was prepared by interesterification of 76.7 g of glycerides rich in cis9, trans 11 CLA acids as prepared in example 7, with 1423 g of sunflower oil using 74 g of *Rhizomucor miehei* immobilised onto Duolite as catalyst. The reaction was carried out at 60° C. for 7 hours. The enzyme was removed by filtration. The resultant product rich in triglycerides containing cis9, trans 11 CLA acids was silica treated to remove partial glycerides The FAME results of the in(Sunflower oil/C9T11 CLA) are listed in table 4.

One large batch of aqueous phase was manufactured and used for all the dressings. The water and maltodextrin were first blended using a Silverson mixer. The egg yolk, xanthum gum and vinegar were sequentially added whilst continuing to stir with the Silverson until complete mixing had occurred. At this stage the pH=3.25 therefore no further adjustment to the pH was made.

The oils were slowly added to the aqueous phase whilst mixing using the Silverson. Mixing was continued until all the oil appeared to have been dispersed. The dressings were then transferred to 200 ml plastic sterile bottles.

The viscosities of the samples were determined using a Brookfield Viscometer fitted with a number 4 spindle rotating at 10 rpm. The samples were contained in identical 200 ml plastic bottles hence the viscosities are directly comparable with each other. For each sample the average of three measurements was taken with the sample being allowed to relax for 1 minute between each 1 minute of shear.

The oil droplet size distribution was determined using a Malvern Mastersizer using a 45 mm filter.

Evaluation results for the dressings

| OIL | VISCOSITY cP | SAUTER MEAN PARTICLE DIAMETER μM |
|---|---|---|
| Reference | 4320 | 2.84 |
| in(Sunflower oil/C9T11 CLA) | 3993 | 2.90 |

Example 17

Ranch style dressings incorporating glycerides rich in the trans 10, cis 12 isomer of CLA, as made in example 8, were prepared according to the following recipe:

|  | wt % |
|---|---|
| Liquid oil | 25.0 |
| Maltodextrin | 20.0 |
| Dried egg yolk | 0.8 |
| Xanthum gum | 0.4 |
| Vinegar | 5.0 |
| Water | 48.8 |

In above recipe two-different liquid oils were applied. The liquid oil for the reference was Sunflower oil and the liquid oil according to the invention was a blend of glycerides rich in the trans 10, cis 9 isomer which were prepared as described in example 8 with sunflower oil, Sunflower oil/T10C12 CLA 95/5

The FAME results of the T10C12 CLA are listed in table 4.

One large batch of aqueous phase was manufactured and used for all the dressings. The water and maltodextrin were first blended using a Silverson mixer. The egg yolk, xanthum gum and vinegar were sequentially added whilst continuing to stir with the Silverson until complete mixing had occurred. At this stage the pH=3.25 therefore no further adjustment to the pH was made.

The oils were slowly added to the aqueous phase whilst mixing using the Silverson. Mixing was continued until all the oil appeared to have been dispersed. The dressings were then transferred to 200 ml plastic sterile bottles.

The viscosities of the samples were determined using a Brookfield Viscometer fitted with a number 4 spindle rotating at 10 rpm. The samples were contained in identical 200 ml plastic bottles hence the viscosities are directly comparable with each other. For each sample the average of three measurements was taken with the sample being allowed to relax for 1 minute between each 1 minute of shear.

The oil droplet size distribution was determined using a Malvern Mastersizer using a 45 mm filter.

Evaluation results for the dressings

| OIL | VISCOSITY cP | SAUTER MEAN PARTICLE DIAMETER μM |
|---|---|---|
| Reference | 4320 | 2.84 |
| Sunflower oil/T10C12 CLA | 3940 | 2.80 |

Example 18

SOCLA was prepared as described in example 6. The results of the gas chromatography analysis of the fatty acid methyl esters were as follows. The product contained 63.8% CLA of which 48.9% was the cis 9, trans 10 isomer and 51.1% was the trans 10, cis 12 isomer.

SOCLA fatty acids were converted to their ethyl esters as follows: 50 g of SOCLA fatty acids was mixed with 150 ml dry ethanol to which was added 10 ml concentrated HCl. The mixture was refluxed under nitrogen for 23 hours, cooled and stirred with basic alumina to remove unreacted FFA. The alumina was filtered off and the reaction mixture washed 4 times with water and dried. The resultant oil (40 g) was determined to be 91% ethyl esters.

The ethyl esters prepared above were selectively hydrolysed as follows: 0.2 mg of *Candida rugosa* lipase was dissolved in 2 ml distilled water and mixed with 1 g of SOCLA ethyl esters. The reaction temperature was held at 30° C. and the mixture shaken vigorously for 0.5 hours. The mixture was extracted with a 1:1 solution of dichloromethane and petroleum ether, which was subsequently removed by evaporation. The product contained 19.1% FFA which was separated from the ethyl esters by thin layer chromatography. Gas chromatography analysis showed that the FFA fraction contained 45.6% cis 9 CLA isomer and 9.7% trans 10 CLA isomer.

Example 19

SOCLA was prepared as described in example 6. The results of the gas chromatography analysis of the fatty acid methyl esters were as follows. The product contained 63.8 % CLA of which 48.9% was the cis 9, trans 10 isomer and 51.1% was the trans 10, cis 12 isomer.

SOCLA fatty acids were converted to their methyl esters as follows: 50 g of SOCLA fatty acids was mixed with 200 ml dry methanol to which was added 10 ml concentrated HCl. The mixture was refluxed under nitrogen for 26 hours, cooled and stirred with basic alumina to remove unreacted FFA. The alumina was filtered off and the reaction mixture washed 3 times with water and dried. The resultant oil (40 g) was determined to be 99% methyl esters.

The methyl esters prepared above were selectively hydrolysed as follows: 10 mg of *Candida rugosa* lipase was dissolved in 4 ml distilled water and mixed with 1 g of SOCLA methyl esters. The reaction temperature was held at 30° C. and the mixture shaken vigorously for 0.7 hours. The mixture was extracted with a 1:1 solution of dichloromethane and petroleum ether, which was subsequently removed by evaporation. The. product contained 24.4% FFA which was separated from the methyl esters and collected using thin layer chromatography. Gas chromatography analysis showed that the FFA fraction contained 46.6% cis 9 CLA isomer and 10.8% trans 10 CLA isomer.

Example 20

Methyl esters of SOCLA were prepared and selectively hydrolysed using *Candida rugosa* lipase as described in example 19 above. After 1 hour reaction time the reaction mixture, which contained 38% FFA, was extracted and the methyl esters were separated from the FFA and collected by TLC as described in example 19. Gas chromatography analysis showed that the methyl esters contained 15.3% cis 9 CLA isomer and 38.2% trans 10 CLA isomer.

TABLE 1a

Results of FAME GC and HPLC analyses of experiment 7 before molecular distillation.

|  | mono-glycerides | di-glycerides | tri-glycerides | free fatty acids |
|---|---|---|---|---|
| Partial glyceride content | 13.3% | 17.4% | 11.3% | 58.0% |
| Ratio of CLA isomers |  |  |  |  |
| CLA C9T11 | 75.8% | 73.6% | 76.0% | 36.9% |
| CLA T10C12 | 24.2% | 26.4% | 24.0% | 63.1% |

TABLE 1b

Results of FAME GC and HPLC analyses of experiment 7 after molecular distillation.

|  | FFA fraction | | | | Partial glyceride fraction | | | |
|---|---|---|---|---|---|---|---|---|
|  | FFA | Monogl | Digly | Trigl | FFA | Monogl | Digly | Trigl |
| Partial glyceride content | 91.5 | 8.5 | 0.0 | 0.0 | 5.3 | 21.7 | 44.5 | 28.5 |
| Ratio of CLA isomers |  |  |  |  |  |  |  |  |
| CLA C9T11 |  | 40.6 |  |  |  | 73.8 |  |  |
| CLA T10C12 |  | 59.4 |  |  |  | 26.2 |  |  |

TABLE 2

N-values of the blends.

| Application | Blend | N-5 n.s. (%) | N-10 n.s. (%) | N-20 n.s. (%) | N-35 n.s. (%) |
|---|---|---|---|---|---|
| Chocolate | Typical values | 85–95 | 80–95 | 55–65 | <1 |
|  | 99/1 CCB/C9T11 | 92.3 | 88.9 | 58.2 | 0.4 |
| Bakery | Typical values | 40–80 | 30–75 | 20–45 | <15 |
|  | 40/50/10 POf37/dfPOf/C9T11 | 54.5 | 47.7 | 24.9 | 2.2 |
| Ice cream coatings | Typical values | 65–90 | >35 | >15 | <1 |
|  | 90/5/5 CN/CNs/C9T11 | 83.5 | 75.9 | 32.2 | 0.5 |
| Ice cream | Typical values | 40–60 |  | 15–30 | <5 |
|  | 90/10 PO/C9T11 | 52.8 |  | 21.7 | 4.5 |
| Non dairy creams | Typical values | 1–70 |  | 0–37 | 0–11 |
|  | 40/40/20 nPOm/dfPOf/C9T11 | 51.6 |  | 13.2 | 1.0 |
| Health margarines/Health spreads | Typical values | 7–20 |  | 3–12 | <2.5 |
|  | 13/77/10 HSB1/S/C9T11 | 13.8 |  | 9.1 | 2.4 |
| Confectionery filling | Typical values | >50 | >40 | >25 | <1 |
|  | 60/20/20 nPOm/dfPOf/C9T11 | 68.1 | 61.9 | 35.6 | 0.0 |
| Mayonnaise/Sauces | Typical values | 0–10 | 0–5 | <1 | <0.5 |
|  | 90/10 S/C9T11 | 0.6 | 0.5 | 0.3 | 0.2 |
| Dressings | Typical values | 0–10 | 0–5 | <1 | <0.5 |
|  | 90/10 S/C9T11 | 0.6 | 0.5 | 0.3 | 0.2 |

TABLE 3

N-values of the blends.

| Application | Blend | N-5 n.s. (%) | N-10 n.s. (%) | N-20 n.s. (%) | N-35 n.s. (%) |
|---|---|---|---|---|---|
| Chocolate | Typical values | 85–95 | 80–95 | 55–65 | <1 |
|  | 99/1 CCB/T10C12 | 92.1 | 89.0 | 60.1 | 0.6 |
| Bakery | Typical values | 40–80 | 30–75 | 20–45 | <15 |
|  | 40/50/10 POf37/dfPOf/T10C12 | 45.8 | 50.1 | 26.2 | 2.3 |
| Ice cream coatings | Typical values | 65–90 | >35 | >15 | <1 |
|  | 90/5/5 CN/CNs/T10C12 | 82.6 | 77.8 | 33.7 | 0.9 |
| Ice cream | Typical values | 40–60 |  | 15–30 | <5 |
|  | 90/10 PO/T10C12 | 53.5 |  | 22.2 | 3.1 |
| Non dairy creams | Typical values | 1–70 |  | 0–37 | 0–11 |
|  | 40/40/20 nPOm/dfPOf/T10C12 | 51.5 |  | 14.0 | 0.0 |

TABLE 3-continued

N-values of the blends.

| Application | Blend | N-5 n.s. (%) | N-10 n.s. (%) | N-20 n.s. (%) | N-35 n.s. (%) |
|---|---|---|---|---|---|
| Health margarines/ Health spreads | Typical values | 7–20 | | 3–12 | <2.5 |
| | 13/77/10 HSB1/S/ T10C12 | 15.3 | | 9.1 | 2.3 |
| Confectionery filling | Typical values | >50 | >40 | >25 | <1 |
| | 60/20/20 nPOm/ dfPOf/T10C12 | 69.9 | 63.3 | 35.8 | 0.4 |
| Mayonnaise/ Sauces | Typical values | 0–10 | 0–5 | <1 | <0.5 |
| | 90/10 S/T10C12 | 1.4 | 0.9 | 0.1 | 0.1 |
| Dressings | Typical values | 0–10 | 0–5 | <1 | <0.5 |
| | 90/10 S/T10C12 | 1.4 | 0.9 | 0.1 | 0.1 |

TABLE 4

FATTY ACID DISTRIBUTION OF CLA CONTAINING FATS USED IN EXAMPLES 14 TO 17

| | in (SUNFLOWER OIL/ C9,T11 CLA) | FAT PHASE SPREADS EXAMPLE 14 | T10,C12 CLA | FAT PHASE SPREADS EXAMPLE 15 |
|---|---|---|---|---|
| C8:9 | 0 | .2 | 0 | 0.1 |
| C10:0 | 0 | .2 | 0 | 0.1 |
| C12:0 | 0 | 2.9 | 0 | 2.7 |
| C14:0 | 0.1 | 1.2 | 0.1 | 1.1 |
| C16:0 | 5.7 | 7.9 | 4.8 | 7.9 |
| C1601 | 0.1 | .1 | 0.1 | 0.1 |
| C18:0 | 3.5 | 8.6 | 5.1 | 8.3 |
| C18:1 | 23.9 | 21.0 | 17.0 | 21.4 |
| C18:2 | 63.2 | 55.2 | 1.1 | 54.6 |
| C18:3 | 0 | 0.1 | 0 | 0.1 |
| C2050 | 0.2 | 0.2 | 0 | 0.2 |
| C20:1 | 0.2 | 0.2 | 0 | 0.2 |
| C22:0 | 0.6 | 0.5 | 1.5 | 0.6 |
| C22:1 | 0 | 0 | 0 | 0 |
| C24:0 | 0 | 0 | 0.5 | 0 |
| CLA09C,11T | 1.9 | 1.4 | 19.8 | 0.7 |
| CLA 10T,12C | 0.7 | 0.5 | 44.8 | 1.9 |
| other | | | 4.8 | |

What is claimed is:

1. An oral composition having at least one property selected from the group consisting of viscosity, droplet size and hardness comparable to a similar product based on sunflower oil, comprising acylglycerol compounds having substituents $R_1$, $R_2$ and $R_3$ attached at the positions of the $OH^-$ groups of a glycerol backbone; wherein:

(a) $R_1$ and $R_2$ are conjugated linoleic acid, and (b) $R_3$ is selected from the group consisting of conjugated linoleic acid and OH;

and wherein the oral composition is substantially free of free conjugated polyunsaturated fatty acids and monoacylglycerol compounds, said acylglycerol compounds comprising geometrical isomers $L_1$ and $L_2$ of conjugated linoleic acid moieties wherein the weight ratio of $L_1$ to $L_2$ or vice versa is at least 1.1.

2. An oral composition comprising acylglycerol compounds having substituents $R_1$, $R_2$ and $R_3$ attached at the positions of the $OH^-$ groups of a glycerol backbone; wherein:

(a) $R_1$ and $R_2$ are conjugated linoleic acid, and (a) $R_3$ is selected from the group consisting of conjugated linoleic acid and OH;

and wherein the oral composition is substantially free of free conjugated polyunsaturated fatty acids and monoacylglycerol compounds, said acylglycerol compounds comprising geometrical isomers $L_1$ and $L_2$ of conjugated linoleic acid moieties wherein the weight ratio of $L_1$ to $L_2$ or vice versa is at least 1.1.

3. An oral composition according to claim 2 wherein $R_3$ is conjugated linoleic acid.

4. An oral composition according to claim 2 wherein said or composition is a food composition.

* * * * *